United States Patent [19]
Li et al.

[11] Patent Number: 6,100,414
[45] Date of Patent: Aug. 8, 2000

[54] CYCLOPENTADIENYL TRANSITION METAL COMPOUNDS USEFUL AS POLYMERIZATION CATALYSTS

[75] Inventors: Robert Tan Li, Houston; Laughlin Gerard McCullough, League City, both of Tex.

[73] Assignee: Eastman Chemical Company, Kingsport, Tenn.

[21] Appl. No.: 09/053,924

[22] Filed: Apr. 2, 1998

[51] Int. Cl.⁷ ............................... C07F 17/00; C07F 7/00
[52] U.S. Cl. ................... 556/11; 556/7; 556/8; 556/12; 556/21; 556/28; 556/53; 502/103; 502/117; 526/126; 526/160; 526/943
[58] Field of Search ................ 556/11, 12, 21, 556/7, 8, 28, 53; 502/103, 117; 526/160, 126, 943

[56] References Cited

U.S. PATENT DOCUMENTS

| | | | |
|---|---|---|---|
| 4,404,344 | 9/1983 | Sinn et al. | 526/160 |
| 4,542,199 | 9/1985 | Kaminsky et al. | 526/160 |
| 4,752,597 | 6/1988 | Turner | 502/104 |
| 4,978,730 | 12/1990 | Maezawa et al. | 526/153 |
| 5,023,222 | 6/1991 | Maezawa et al. | 502/103 |
| 5,045,517 | 9/1991 | Campbell, Jr. et al. | 502/103 |
| 5,066,741 | 11/1991 | Campbell, Jr. | 526/171 |
| 5,196,490 | 3/1993 | Campbell, Jr. et al. | 526/160 |
| 5,198,401 | 3/1993 | Turner et al. | 502/155 |
| 5,278,119 | 1/1994 | Turner et al. | 502/155 |
| 5,340,892 | 8/1994 | Kuramoto | 526/119 |
| 5,453,475 | 9/1995 | Rieger et al. | 526/160 |
| 5,554,795 | 9/1996 | Frey et al. | 568/8 |
| 5,563,284 | 10/1996 | Frey et al. | 556/53 |
| 5,565,396 | 10/1996 | Frey et al. | 502/113 |
| 5,578,741 | 11/1996 | Frey et al. | 585/360 |
| 5,591,874 | 1/1997 | Puckette et al. | 549/507 |

FOREIGN PATENT DOCUMENTS

| | | |
|---|---|---|
| 196 02 543 | 7/1997 | Germany. |
| WO 96/13529 | 5/1996 | WIPO. |
| WO 97 42228 | 11/1997 | WIPO. |

OTHER PUBLICATIONS

Boris Bosch et al, Chemical Abstracts, vol. 128, No. 1, Jan. 5, 1998.
Axel Bertuleit et al, Chemical Abstracts, vol. 127, No. 2, Jul. 14, 1997.
Francisco Amor et al, Chemical Abstracts, vol. 130, No. 11, Mar. 15, 1999.
James R. Butchard et al, J. Organomet. Chem. (1997) 541, 407–416.
Ying Mu et al, Can. J. Chem. (1996) 74(9), 1696–1703.
S. Strauss et al., *Chem. Rev.* 1993, 93, 927.

*Primary Examiner*—Porfirio Nazario-Gonzalez
*Attorney, Agent, or Firm*—Jonathan D. Wood; Bernard J. Graves, Jr.; Harry J. Gwinnell

[57] ABSTRACT

Disclosed are novel cyclopentadienyl transition metal compounds that are stable under a wide variety of conditions, particularly under conditions that include exposure to water and oxygen containing media. These novel compounds can be utilized in preparing novel catalyst systems useful in polymerizing olefins. The cyclopentadienyl compound can specifically be [(C5H4CH2CH2N[H]Me2)TiCl3]+B[C6F5]4-. Also disclosed are processes for preparing the novel cyclopentadienyl transition metal compounds.

50 Claims, No Drawings

CYCLOPENTADIENYL TRANSITION METAL COMPOUNDS USEFUL AS POLYMERIZATION CATALYSTS

FIELD OF THE INVENTION

The present invention relates to novel cyclopentadienyl transition metal compounds, methods for producing the cyclopentadienyl transition metal compounds; utilization of the cyclopentadienyl compounds in the preparation of catalyst systems; the polymerization or copolymerization of olefins utilizing the catalyst systems, and the polymers produced thereby.

BACKGROUND OF THE INVENTION

Many catalytic processes exist for the polymerization or copolymerization of olefins such as ethylene and propylene. These processes have traditionally utilized a Ziegler-Natta catalyst system. These catalyst systems contain a transition metal compound (typically a titanium, zirconium, or vanadium halide or alkoxide) and a main group metal alkyl (usually an aluminum alkyl). The Ziegler-Natta catalyst systems are heterogeneous and possess a number of different active catalyst sites. Each different active site has different characteristics and produces a different polymer, and as a result, Ziegler-Natta catalyst systems produce polyolefins with broad molecular weight distributions and copolymers with broad compositional distributions.

Recent developments in the field of olefin polymerization have focused on the use of transition metal compounds having at least one π-bound cyclopentadienyl ligand. The cyclopentadienyl ligand can be substituted or unsubstituted, and generally includes fused ring derivatives such as indenyl and fluorenyl. These cyclopentadienyl transition metal compounds are often referred to as metallocenes, though the term was initially used to describe biscyclopentadienyl compounds such as dicyclopentadienyliron (ferrocene).

Olefin polymerization systems using metallocenes differ from Ziegler-Natta catalyst systems in important ways. With metallocene catalysts, there is generally only one catalytically active species responsible for the polymerization of the monomers. The metallocenes, therefore, produce uniform chains of polymer having narrower molecular weight distributions and narrower compositional distribution. Metallocene catalysts are also typically much more active on a weight basis than Ziegler-Natta catalysts. Metallocene catalysts can be 10 to 1,000 times more active than the best Ziegler-Natta catalysts.

Metallocene catalysts are often classified into two separate groups, those possessing one cyclopentadienyl ligand, and those possessing two cyclopentadienyl ligands. The monocyclopentadienyl metallocenes are generally known in the art as good styrene polymerization catalysts and poor olefin polymerization catalysts, whereas biscyclopentadienyl metallocenes are generally known in the art as good olefin polymerization catalysts and poor styrene polymerization catalysts. Representative examples of these various catalysts are disclosed in the PCT patent application WO 96/13529; U.S. Pat. Nos. 4,978,730; 5,023,222; 5,045,517; 5,066,741; 5,196,490; 5,340,892; 5,554,795; 5,563,284; 5,565,396; 5,578,741; 5,591,874, and German AS 19602543.5, disclosing monocyclopentadienyl metallocenes. Examples of biscyclopentadienyl metallocenes are disclosed in U.S. Pat. Nos. 4,404,344; 4,542,199; 4,752,597; 5,198,401; 5,278,119; and 5,453,475.

However, many of the known metallocene catalysts are unstable under a variety of conditions, particularly when those conditions include exposure to water- or oxygen-containing media. This exposure can occur as a result of minor amounts of contaminants already present in the system, or later inadvertent exposure. This results in the decomposition and/or deactivation of the metallocene catalyst producing less than optimum productivity as well as erratic productivity. Due to this decomposition and/or deactivation, extreme handling conditions are required. This special handling adds to the final cost of these very expensive catalysts, making them less desirable in commercial polymerization processes.

In light of the above, it would be very desirable to have metallocene catalysts that are stable under a wide variety of conditions, particularly under conditions that include exposure to water or oxygen containing media.

SUMMARY OF THE INVENTION

According to the present invention, there is provided a novel cyclopentadienyl transition metal compound of the formula:

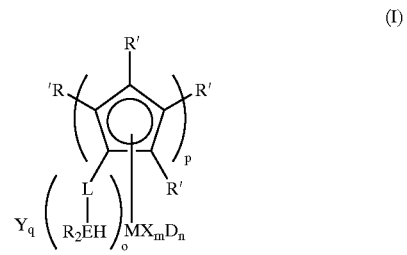

(I)

wherein,

M is a Group IV metal selected from the group consisting of titanium, zirconium, and hafnium;

R' is each independently selected from the group consisting of hydrogen, hydrocarbyl groups, silyl groups, germyl groups, stannyl groups, and groups wherein two or more R' groups can be joined to form a ring;

L is a covalent bridging group containing a Group 14 element selected from the group consisting of carbon, silicon, germanium, and tin;

E is a Group 15 element selected from the group consisting of nitrogen, phosphorous, arsenic, and antimony;

Y is an anion that results in the cyclopentadienyl transition metal compound being hydrocarbon soluble;

R is each independently selected from the group consisting of hydrocarbyl groups, silyl groups, groups wherein two R groups can be joined to form a ring, and groups wherein an L group and an R group can be joined to form a ring;

X is each independently selected from the group consisting of hydrogen, halides, hydrocarbyl groups, silyl groups, alkoxides, aryloxides, amides, arylamides, phosphates, arylphosphides, carboxylates, and sulfonates;

D is a neutral Lewis base;

m is one, two, or three, depending on the valency and oxidation state of M;

n is 0, 1,or 2;

o is 1 or 2;

p is 1 or 2;

q is 1 or 2; and $1 \leq q \leq p \leq o \leq 2$.

The present invention is also directed to a process for producing the novel cyclopentadienyl transition metal compounds of formula (I) by reacting a compound of the following formula (II):

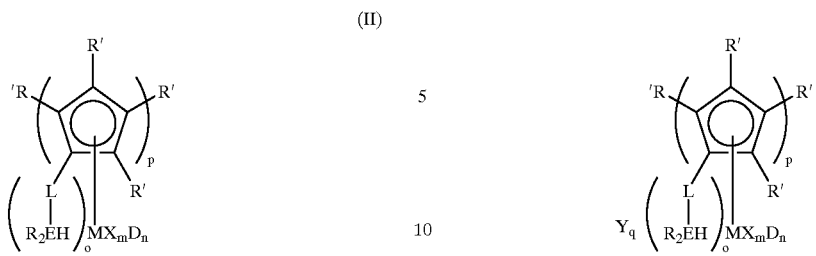

(II)

(I)

wherein M, R', L, E, R, X, D, m, n, o, and p are as defined above, with a Bronsted acid having a non-coordinating or weakly-coordinating anion thereby producing a stable cyclopentadienyl transition metal compound of formula (I).

The present invention is also directed to a preferred two-step process for producing the novel cyclopentadienyl transition metal compounds of formula (I) by reacting a compound of formula (II) with any Bronsted acid to form a resulting material that is reacted with a salt of a non-coordinating or weakly-coordinating anion thereby producing a stable, hydrocarbon soluble cyclopentadienyl transition metal compound of formula (I).

The present invention is also directed to a novel catalyst system comprising (A) a novel cyclopentadienyl transition metal compound of formula (I), preferably a monocyclopentadienyl transition metal compound, and (B) an activator selected from (1) alumoxanes, (2) a salt of a labile, non-coordinating or weakly-coordinating anion that can abstract one substituent X from the compound of formula (I), (3) a neutral Lewis acid that can abstract one substituent X from the compound of formula (I), (4) an organometallic compound wherein the metal is selected from the group consisting of lithium, sodium, potassium, magnesium, calcium, zinc, boron and aluminum, and (5) mixtures of B(1) through B(4).

The present invention is also directed to a process for polymerizing or copolymerizing olefins comprising contacting at least one olefin with the above described novel catalyst system and recovering the polyolefin.

The terms non-coordinating or weakly-coordinating anions, as used herein, describe anions that either do not, or do only weakly coordinate to a cyclopentadienyl group containing cation, thereby remaining sufficiently labile to be displaced by a neutral Lewis base. Suitable weakly coordinating anions include, but are not limited to, $PF_6^-$, $BF_4^-$, $SbF_6^-$, $(Ph)_4B^-$ (where Ph=phenyl), $BAr_4^-$ (tetrakis[3,5-bis (trifluoromethyl)phenyl]borate, and tetrakis (perfluorophenyl)borate. The coordinating ability of such anions is known per se. See S. Strauss et al., *Chem. Rev.* 1993, 93, 927.

DETAILED DESCRIPTION OF THE INVENTION

The applicants have unexpectedly discovered a novel stable cyclopentadienyl transition metal compound that is very useful in catalyst systems for the polymerization of olefins.

The novel cyclopentadienyl transition metal compound of the present invention comprises a cyclopentadienyl transition metal compound of the formula:

wherein,

M is a Group IV metal selected from the group consisting of titanium, zirconium, and hafnium;

R' is each independently selected from the group consisting of hydrogen, hydrocarbyl groups, silyl groups, germyl groups, stannyl groups and groups wherein two or more R' groups can be joined to form a ring;

L is a covalent bridging group containing a Group 14 element selected from the group consisting of carbon, silicon, germanium, and tin;

E is a Group 15 element selected from the group consisting of nitrogen, phosphorous, arsenic, and antimony;

Y is an anion that results in the cyclopentadienyl transition metal compound being hydrocarbon soluble;

R is each independently selected from the group consisting of hydrocarbyl groups, silyl groups, groups wherein two R groups can be joined to form a ring, and groups wherein an L group and an R group can be joined to form a ring;

X is each independently selected from the group consisting of hydrogen, halides, hydrocarbyl groups, silyl groups, alkoxides, aryloxides, amides, arylamides, phosphides, arylphosphides, carboxylates, and sulfonates;

D is a neutral Lewis base;

m is one, two, or three, depending on the valency and oxidation state of M;

n is 0, 1 or 2;

o is 1 or 2;

p is 1 or 2;

q is 1 or 2; and $1 \leq q \leq p \leq o \leq 2$.

Since o can be one or two, the cyclopentadienyl transition metal compound of the present invention can contain one or two cyclopentadienyl ligands that can be unsubstituted or substituted. Thus the cyclopentadienyl transition metal compound of the present invention can be a monocyclopentadienyl or biscyclopentadienyl transition metal compound. This includes substituted cyclopentadienyl ligands in which the substituents form a fused aliphatic or aromatic ring or rings. This broad description thus includes indenyl transition metal compounds, fluorenyl transition metal compounds, and benzindenyl transition metal compounds.

The transition metal M of the cyclopentadienyl transition metal compound of the present invention is a Group IV metal selected from the group consisting of titanium, zirconium, and hafnium, more preferably titanium and zirconium, with titanium being most preferred.

In the cyclopentadienyl transition metal compound of the formula (I), o is preferably one. Accordingly, the cyclopentadienyl of the cyclopentadienyl transition metal compound of formula (I) is preferably a monocyclopentadienyl. In the preferred monocyclopentadienyl transition metal compound of the present invention, m is preferably two or three, with m being three most preferred.

In the compound of formula (I), R' is each independently selected from the group consisting of hydrogen, hydrocarbyl groups, silyl groups, germyl groups, stannyl groups, and groups wherein two or more R' groups can be joined to form a ring. Preferably, R' is each independently selected from the group consisting of hydrogen and $C_1$–$C_4$ alkyls. Preferably, at least one R' group is hydrogen, and more preferably, at least two R' groups are hydrogen. Furthermore, each R' being hydrogen is most preferred when cost is the most important factor, since the cost of preparing a compound in which each R' is hydrogen is significantly lower than the cost of preparing a compound in which R' is an alkyl.

In the cyclopentadienyl transition metal compound of formula (I), L is a covalent bridging group selected from the group consisting of $CR''_2$, $CR''_2CR''_2$, $CR''_2CR''_2CR''_2$, $CR''{=}CR''$. L is preferably selected from the group consisting of $CR''_2$, $CR''_2CR''_2$, and $CR''_2CR''_2CR''_2$, with $CR''_2CR''_2$ being most preferred. R'' is each independently selected from the group consisting of hydrogen, $C_1$–$C_{14}$ alkyl, and $C_1$–$C_{14}$ aryl, with hydrogen and methyl being preferred, with hydrogen being most preferred.

In the cyclopentadienyl transition metal compound of formula (I), E is a Group 15 element selected from the group consisting of nitrogen, phosphorous, arsenic, and antimony; preferably nitrogen and phosphorous, with nitrogen being most preferred.

In the cyclopentadienyl transition metal compound of formula (I), Y is an anion that results in the compound of formula (I) being hydrocarbon soluble. Suitable examples of Y anions include tetrakis(pentafluorophenyl)borate, tetrakis[3,5-(bistrifluoromethyl)phenyl]borate, tetrakis(2,3,4,5-tetrafluorophenyl)borate, and tetrakis(2,3,5,6-tetrafluorophenyl)borate, with tetrakis(pentafluorophenyl)borate being most preferred.

In the compounds of formula (I), when both o and p are 2, q is 1, and both E's are protonated, Y may be either a monoanion or a dianion.

The two R groups attached to E are each independently selected from the group consisting of hydrocarbyl groups, silyl groups, groups wherein two R groups can be joined to form a ring, and groups wherein an R group and an L group can be joined to form a ring. The two R groups attached to E are each preferably $C_1$–$C_4$ alkyl, with each R group most preferably being methyl.

The X in the cyclopentadienyl transition metal compound of formula (I) is each independently selected from the group consisting of hydrogen, halides, hydrocarbyl groups, silyl groups, alkoxides, aryloxides, amides, arylamides, phosphides, arylphosphides, carboxylates, and sulfonates. X is more preferably selected from halides or alkoxides, with chlorine and isopropoxide being the most preferred.

In the cyclopentadienyl transition metal compound of formula (I), D which is optionally present, is a neutral Lewis base, and is preferably selected from the group consisting of ethers and tetrahydrofuran. As stated above, n can be zero, one, two, or three, with zero being most preferable.

Examples of the preferred cyclopentadienyl transition metal compounds of formula (I) include $[(C_9H_6CH_2CH_2N[H]Me_2)TiCl_3]^+Y^-$; $[(C_5H_4CH_2CH_2N[H]Et_2)TiCl_3]^+Y^-$; $[(C_5H_4CH_2CH_2N[H]Me_2)Ti(OCHMe_2)_3]^+Y^-$; and $[(C_5H_4CH_2CH_2N[H]Me_2)TiCl_3]^+Y^-$; with $[(C_5H_4CH_2CH_2N[H]Me_2)TiCl_3]^+Y^-$ being most preferred, wherein Y is as defined above, but is most preferably tetrakis(pentafluorophenyl)borate.

The cyclopentadienyl compound of formula (I) can be prepared by reacting a cyclopentadienyl compound of formula (II) with a Bronsted acid having a non-coordinating or weakly-coordinating anion. In general, the compound of formula (I) can be prepared by reacting the two components in a suitable solvent at a temperature ranging from about $-100°$ C. to about $300°$ C., preferably from about $25°$ C. to about $100°$ C. Examples of suitable Bronsted acids having a non-coordinating or weakly-coordinating anion include $HB[3,5\text{-}(CF_3)C_6H_2]_4$, $HB(C_6F_5)_4$, $HB(2,3,4,5\text{-}(F)C_6H)_4$, $HB(2,3,5,6\text{-}(F)C_6H)_4$, $HB(3,4,5\text{-}(F)C_6F_2)_4$, $C_6H_5NH_3\text{—}B(C_6F_5)_4$, with the most preferred being $HB[3,5\text{-}(CF_3)C_6H_2]_4$, $HB(C_6F_5)_4$, and $C_6H_5NH_3\text{—}B(C_6F_5)_4$. Examples of suitable solvents include halogenated solvents such as dichloromethane, chloroform and the like; aromatic solvents such as benzene, toluene, xylene and the like; ether-containing solvents such as diethyl ether, tetrahydrofuran, dioxane, dimethoxyethane and the like; with the most preferred being the halogenated solvents.

The cyclopentadienyl compound of formula (I) can also be prepared by first reacting the cyclopentadienyl compound of formula (II) with a Bronsted acid in a suitable solvent at a temperature ranging from about $-100°$ C. to about $300°$ C., preferably from about $25°$ C. to about $100°$ C., to form an intermediate product of formula:

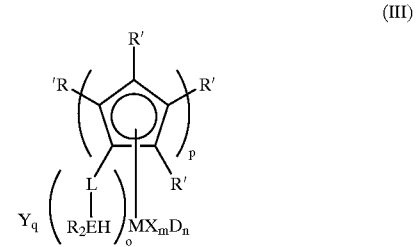

(III)

wherein,

M is a Group IV metal selected from the group consisting of titanium, zirconium, and hafnium;

R' is each independently selected from the group consisting of hydrogen, hydrocarbyl groups, silyl groups, germyl groups, stannyl groups and groups wherein two or more R' groups can be joined to form a ring;

L is a covalent bridging group containing a Group 14 element selected from the group consisting of carbon, silicon, germanium, and tin;

E is a Group 15 element selected from the group consisting of nitrogen, phosphorous, arsenic, and antimony;

Y is an anion;

R is each independently selected from the group consisting of hydrocarbyl groups, silyl groups, groups wherein two R groups can be joined to form a ring, and groups wherein an L group and an R group can be joined to form a ring;

X is each independently selected from the group consisting of hydrogen, halides, hydrocarbyl groups, silyl groups, alkoxides, aryloxides, amides, arylamides, phosphides, arylphosphides, carboxylates, and sulfonates;

D is a neutral Lewis base;

m is one, two, or three, depending on the valency and oxidation state of M;

n is 0, 1 or 2;

o is 1 or 2;

p is 1 or 2;

q is 1 or 2; and $1 \leq q \leq p \leq o \leq 2$.

Examples of suitable solvents include halogenated solvents such as dichloromethane, chloroform and the like; aromatic solvents such as benzene, toluene, xylene and the like; ether-containing solvents such as diethyl ether, tetrahydrofuran, dioxane, dimethoxyethane and the like; with the most preferred being the halogenated solvents. This intermediate product of formula (III) is then reacted with a salt of a non-coordinating or weakly-coordinating anion in a suitable solvent at a temperature ranging from about −100° C. to about 300° C., preferably from about 25° C. to about 100° C. Exemplary suitable Bronsted acids include hydrogen halides, hydrogen sulfates, hydrogen phosphates, hydrogen nitrates and the like; preferred Bronsted acids are the hydrogen halides. Suitable salts of non-coordinating or weakly-coordinating anions include triphenylcarbenium tetrakis(pentafluorophenyl)borate, sodium tetrakis(pentafluorophenyl)borate, lithium tetrakis(pentafluorophenyl)borate, triphenylcarbenium benzyltris(pentafluorophenyl)borate, sodium benzyltris(pentafluorophenyl)borate, triphenylcarbenium phenyltris(pentafluorophenyl)borate, sodium phenyltris(pentafluorophenyl)borate, triphenylcarbenium methyltris(pentafluorophenyl)borate, sodium methyltris(pentafluorophenyl)borate, triphenylcarbenium tetrakis(3,5-trifluoromethylphenyl)borate, sodium tetrakis(3,5-trifluoromethylphenyl)borate, triphenylcarbenium tetrakis(2,3,4,5-tetrafluorophenyl)borate, sodium tetrakis(2,3,4,5-tetrafluorophenyl)borate, triphenylcarbenium tetrakis(2,3,5,6-tetrafluorophenyl)borate, sodium tetrakis(2,3,5,6-tetrafluorophenyl)borate, triphenylcarbenium tetrakis(3,4,5-trifluorophenyl)borate, sodium tetrakis(3,4,5-trifluorophenyl)borate, tropylium tetrakis(pentafluorophenyl)borate, sodium tetrakis(pentafluorophenyl)borate, with the most preferred being triphenylcarbenium tetrakis(pentafluorophenyl)borate, sodium tetrakis(pentafluorophenyl)borate, lithium tetrakis(pentafluorophenyl)borate, triphenylcarbenium tetrakis(3,5-trifluoromethylphenyl)borate, and sodium tetrakis(3,5-trifluoromethylphenyl)borate. The resultant product is a compound of formula (I).

The hydrocarbon soluble stable cyclopentadienyl transition metal compound of the formula (I) is preferably prepared by the above described two-step process since the yield obtained using the direct conversion from the compound of formula (II) is lower.

The catalyst system according to the present invention comprises:
(A) a cyclopentadienyl transition metal compound of formula (I) and
(B) an activator selected from the group consisting of
 (1) alumoxanes;
 (2) a salt of a labile, non-coordinating or weakly-coordinating anion that can abstract one substituent X from the compound of (A);
 (3) a neutral Lewis acid that can abstract one substituent X from the compound of (A);
 (4) an organometallic compound wherein the metal is selected from the group consisting of lithium, sodium, potassium, magnesium, calcium, zinc, boron and aluminum; and
 (5) mixtures of B(1) through B(4).

The catalyst system according to the present invention includes an alumoxane, B(1), that is preferably methylalumoxane; or a salt of a labile, non-coordinating or weakly-coordinating anion, B(2), that is preferably selected from the group consisting of borate salts and aluminate salts; or a neutral Lewis acid, B(3), that is preferably selected from the group consisting of boranes and alanes; or an organometallic compound, B(4), wherein the metal is selected from the group consisting of lithium, sodium, potassium, magnesium, calcium, zinc, boron and aluminum, that is preferably selected from the group consisting of alkyl boranes, alkyl aluminums and alkyl zincs, and more preferably, trialkyl aluminums. Specific examples of B(2) borate salts and aluminate salts are triphenylcarbenium tetrakis(pentafluorophenyl)borate, triphenylcarbenium benzyltris(pentafluorophenyl)borate, triphenylcarbenium benzyltris(pentafluorophenyl)borate, triphenylcarbenium phenyltris(pentafluorophenyl)borate, triphenylcarbenium methyltris(pentafluorophenyl)borate, triphenylcarbenium tetrakis(3,5-trifluoromethylphenyl)borate, triphenylcarbenium tetrakis(2,3,4,5-tetrafluorophenyl)borate, triphenylcarbenium tetrakis(2,3,5,6-tetrafluorophenyl)borate, triphenylcarbenium tetrakis(3,4,5-trifluorophenyl)borate, tropylium tetrakis(pentafluorophenyl)borate, tropylium tetrakis(pentafluorophenyl)aluminate and triphenylcarbenium tetrakis(pentafluorophenyl)aluminate. Specific examples of B(3) boranes and alanes are tris(pentafluorophenyl)borane, tris(3,5-trifluoromethylphenyl)borane, tris(2,3,4,5-tetrafluorophenyl)borane, tris(2,3,5,6-tetrafluorophenyl)borane, tris(pentafluorophenyl)alane, and tris(3,5-trifluoromethylphenyl)alane.

In the most preferred catalyst system of the present invention, the Y anion of the cyclopentadienyl transition metal compound of formula (I) is a borate, and the activator is an aluminum alkyl.

In general, the catalyst system can be prepared by reacting components A and B in a suitable solvent at a temperature within a range of from about −100° C. to about 300° C., preferably from about 25° C. to about 200° C. The ratio of components [A]/[B] is in the range of from about $10^0$ to about $10^6$, preferably from about $10^2$ to about $10^5$. The catalyst system may be separately prepared prior to use by reacting, the respective components or may be prepared in situ by reacting the components in the presence of the monomers to be polymerized. It is preferred to form the catalyst in situ due to the exceptionally high catalytic effectiveness of catalysts prepared in this manner. The catalyst system is sensitive to both moisture and oxygen and should be handled and transferred in an inert atmosphere such as nitrogen, argon, or helium.

Suitable solvents for the catalyst system preparation and polymerization include any of the solvents known to be useful as solvents in the polymerization of olefins, diolefins, and acetylenically unsaturated monomers. Suitable solvents include, but are not necessarily limited to, straight and branched-chain hydrocarbons such as isobutane, butane, pentane, hexane, heptane, octane and the like; cyclic and alicyclic hydrocarbons such as cyclohexane, cycloheptane, methylcyclohexane, methylcycloheptane, and the like; and aromatic and alkyl-substituted aromatic compounds such as benzene, toluene, xylene, and the like. Suitable solvents also include liquid olefins which may act as monomers or comonomers including ethylene, propylene, butadiene, cyclopentene, 1-hexene, 3-methyl-1-pentene, 4-methyl-1-pentene, 1-4-hexadiene, 1-octene, 1-decene, styrene, and the like.

The catalyst system according to the present invention can also be supported on suitable inert materials. The support is preferably selected from the group consisting of silica, alumina, carbon black, prepolymer, and magnesium oxide.

The process for producing polyolefins according to the present invention comprises:
(i) Contacting at least one olefin, at a temperature and pressure sufficient to polymerize the olefin, with a catalyst system as described above comprising (A) a cyclopentadienyl transition metal compound of formula (I) and, (B) an activator selected from the group consisting of (1) alumoxanes; (2) a salt of a labile non-coordinating or weakly-coordinating anion that can abstract one substituent X from the compound of A; (3) a neutral Lewis acid that can abstract one substituent X from the compound of A; (4) an organometallic compound wherein the metal is selected from the group consisting of lithium, sodium, potassium, magnesium, calcium, zinc, boron and aluminum; and (5) a mixture of B(1) through B(4), and (ii) recovering the polyolefin.

The present invention also relates to the polyolefin produced by this process.

The polymerization process according to the present invention is preferably conducted at a temperature of from about 0° C. to about 300° C., and at a pressure of from about 1 atmosphere to about 1500 atmospheres, and the reaction time is from about 1 second to about 12 hours.

The polymerization process according to the present invention is suitable for the polymerization of at least one olefin selected from alpha-olefins, cyclic olefins, dienes, and vinyl aromatic monomers. An alpha olefin is preferred, with the $C_2$–$C_8$ alpha olefins being more preferred. In the process according to the present invention, the polymers produced can be homopolymers, copolymers of two olefin monomers, and terpolymers of three or more olefin monomers. For homopolymers, an alpha olefin is preferred, with the $C_2$–$C_8$ alpha olefins being more preferred. Copolymers are preferably produced from ethylene and a $C_3$–$C_8$ alpha olefin; and propylene and a $C_2$–$C_8$ alpha olefin. Terpolymers are preferably produced from ethylene and/or propylene and one or two other $C_2$–$C_8$ alpha olefins.

The following examples are intended to illustrate the present invention, and are not intended to be a limitation upon the reasonable scope thereof. All of the examples were completed under a nitrogen blanket in a MO-20-SSG drybox produced and sold by Vacuum Atmospheres. Toluene and pentane were dried under nitrogen by distillation over Na/K alloy and dichloromethane was dried under nitrogen by distillation over $CaH_2$ prior to use. Methylalumoxane (MAO) and triisobutylaluminum were purchased from Akzo Nobel Chemical Co.; triphenylcarbenium tetrakis (pentafluorophenyl)borate was purchased from Asahi Glass; and all other chemicals were purchased from Aldrich Chemical Co. $M_w$ and $M_n$ measurements were determined by gel permeation chromatography (GPC) using a Waters 150C GPC at 138° C. employing a polystyrene universal calibration standard. $^{13}$C NMR spectra were obtained using a JEOL-300 NMR spectrometer. Melt index ratios were determined by an ASTM D1238, Parameter B, Condition 190/2.16. Density measurements were determined by ASTM 4883.

EXAMPLE 1

In this example, a stable isolable compound was prepared by reacting 2.5 g (8.6 mmol) of (2-dimethylaminoethyl) cyclopentadienyltitanium trichloride with 1.2 g (8.6 mmol) of 2,6-lutidine-hydrochloride. The reaction was accomplished by first dissolving the (2-dimethylaminoethyl) cyclopentadienyltitanium trichloride in 25 mL of dichloromethane and then adding the 2,6-lutidine-hydrochloride as a dry powder. The reaction was conducted at room temperature and was continued for 15 minutes. After this time, an insoluble red-orange precipitate separated from solution. The red-orange precipitate was isolated by filtration, washed twice with 20 mL of dichloromethane and dried in vacuo. Yield of the hydrochloride salt of (2-dimethylaminoethyl) cyclopentadienyltitanium trichloride was 2.7 g (96%).

EXAMPLE 2

In this example, a stable, isolable compound was prepared by reacting 0.61 g (1.9 mmol) of the hydrochloride salt of (2-dimethylaminoethyl)cyclopentadienyltitanium trichloride and 0.92 g (1.9 mmol) of sodium [tetrakis(3,5-bistrifluoromethylphenyl)]borate. The reaction was accomplished by first suspending the hydrochloride salt of (2-dimethylaminoethyl)cyclopentadienyltitanium trichloride in 20 mL of dichloromethane and then adding the sodium [tetrakis(3,5-bistrifluoromethylphenyl)]borate as a dry powder. The reaction was conducted at room temperature for 1 hour. After this time, a fluorescent yellow solution was obtained containing NaCl precipitate. The NaCl was removed by filtration and the solvent was removed from the mother liquor leaving a flaky, yellow solid. This solid was washed three times with 15 mL of pentane and dried in vacuo. 1.95 g (91%) of the yellow solid was recovered having the formula $B[(3,5-CF_3)C_6H_3]_4^-[2-Me_2N^+(H)CH_2CH_2—C_5H_4]TiCl_3$.

EXAMPLE 3

In this example, a stable, isolable compound was by reacting 0.20 g (0.60 mmol) of the hydrochloride salt of (2-dimethylaminoethyl)cyclopentadienyltitanium trichloride and 0.21 g (0.60 mmol) of sodium tetraphenylborate. The reaction was accomplished by first suspending the hydrochloride salt of (2-dimethylaminoethyl) cyclopentadienyltitanium trichloride in 15 mL of dichloromethane and then adding the sodium tetraphenylborate as a dry powder. The reaction was conducted at room temperature for 1 hour. After this time, a yellow solution was obtained containing NaCl precipitate. The NaCl was removed by filtration and the solvent was removed from the mother liquor leaving a yellow solid. This solid was washed three times with 15 mL of pentane and dried in vacuo. 0.37 g (99%) of the yellow solid was recovered having a formula of $B(C_6H_5)_4^-[2-Me_2N^+(H)CH_2CH_2—C_5H_4]TiCl_3$.

EXAMPLE 4

In this example, a stable, isolable compound was prepared by reacting 0.50 g (1.5 mmol) of the hydrochloride salt of (2-dimethylaminoethyl)cyclopentadienyltitanium trichloride and 1.4 g (1.5 mmol) of triphenylcarbenium tetrakis (perfluorophenyl)borate. The reaction was accomplished by first suspending the hydrochloride salt of (2-dimethylaminoethyl)cyclopentadienyltitanium trichloride in 15 mL of dichloromethane and then adding the triphenylcarbenium tetrakis(perfluorophenyl)borate as a dry powder. The reaction was conducted at room temperature for 1 hour. After this time, a fluorescent orange-yellow solution was obtained. The solvent was removed in vacuo leaving an orange-yellow solid. This solid was washed three times with 15 mL of pentane and dried in vacuo. 1.91 g (100%) of the orange-yellow solid was recovered in a 1:1 mixture of triphenylcarbenium chloride and $B(C_6F_5)_4^-[2-Me_2N^+(H)CH_2CH_2—C_5H_4]TiCl_3$.

EXAMPLE 5

In this example, a stable, isolable compound was prepared by reacting 0.25 g (0.9 mmol) of (2-dimethylaminoethyl) cyclopentadienyltitanium trichloride and 0.69 g (0.9 mmol) of anilinium tetrakis(perfluorophenyl)borate. The reaction was accomplished by first dissolving (2-dimethylaminoethyl)cyclopentadienyltitanium trichloride in 5 mL of dichloromethane and then adding the anilinium tetrakis(perfluorophenyl)borate as a dry powder. The reaction was conducted at room temperature for 1 hour. After this time, a fluorescent orange-yellow solution was obtained. The solvent was removed in vacuo leaving an orange-yellow solid. This solid was washed three times with 15 mL of pentane and dried in vacuo. 0.92 g (110%) of the orange-yellow solid was recovered which contains a mixture of $B(C_6F_5)_4^-[2\text{-}Me_2N^+(H)CH_2CH_2\text{—}C_5H_4]TiCl_3$ (33%) and (2-dimethylaminoethyl)cyclopentadienyltitanium trichloride (67%).

EXAMPLE 6

Polymerization of ethylene was carried out in a reactor comprising a 500 mL, screw-capped glass pressure bottle containing magnetic stir bars, under nitrogen. Dry, oxygen-free toluene (200 mL) was charged to the reactor. 1.0 mL of a solution of 12.5% methylalumoxane (MAO) in toluene was added to the toluene in the reactor. A catalyst solution was prepared by dissolving $B[(3,5\text{-}CF_3)C_6H_3]_4^-[2\text{-}Me_2N^+(H)CH_2CH_2\text{—}C_5H_4]TiCl_3$ (9.9 mg, 8.6 μmol) in 4.0 mL of the 12.5% MAO solution in toluene. 5 μL of this solution was injected into the reactor and the reactor was heated to 80° C. The reactor was pressurized to 80 psig with ethylene. At the end of one hour, the ethylene flow was stopped; the reactor was cooled to room temperature, and 100 mL of acidic methanol (1:1 mixture of 3M HCl/methanol) was added to the mixture to form a slurry. After stirring the slurry for 30 minutes, the polymer was filtered, washed with acetone, and dried in a vacuum oven overnight. 5.1 g of polyethylene was recovered having a $M_w$ of 260,500 and a $M_w/M_n$ of 1.71.

EXAMPLE 7

The procedure of Example 6 was repeated except $B(C_6H_5)_4^-[2\text{-}Me_2N^+(H)CH_2CH_2\text{—}C_5H_4]TiCl_3$ (5.3 mg, 8.6 μmol) was used. 5.6 g of polyethylene was recovered having a $M_w$ of 253,500 and a $M_w/M_n$ of 1.95.

EXAMPLE 8

In this example, ethylene was polymerized by first adding dry, oxygen-free toluene (200 mL). 46 mL of triisobutylaluminum was added to the reactor of Example 5. A catalyst solution was prepared by dissolving the 1:1 mixture of triphenylcarbenium chloride and $B(C_6F_5)_4^-[2\text{-}Me_2N^+(H)CH_2CH_2\text{—}C_5H_4]TiCl_3$ (15.3 mg, 12.2 μmol) in 4 mL of toluene. 1.0 mL of this solution was injected into the reactor and the reactor was heated to 80° C. The reactor was then pressurized to 80 psig with ethylene. At the end of one hour, the ethylene flow was stopped; the reactor was cooled to room temperature, and 100 mL of acidic methanol (1:1 mixture of 3M HCl/methanol) was added to form a slurry. After stirring the slurry for 30 minutes, the polymer was filtered, washed with acetone, and dried under vacuum overnight. 2.8 g of polyethylene was recovered having a $M_w$ of 513,200 and $M_w/M_n$ of 2.20.

EXAMPLE 9

In this example, ethylene and 1-octene monomers were copolymerized by first adding dry, oxygen-free toluene (180 mL) and 1-octene (20 mL) to the reactor of Example 5. 1.0 mL of 12.5% methylalumoxane (MAO) solution in toluene was added to the reactor. A catalyst solution was prepared by dissolving $B[(3,5\text{-}CF_3)C_6H_3]_4^-[2\text{-}Me_2N^+(H)CH_2CH_2\text{—}C_5H_4]TiCl_3$ (9.9 mg, 8.6 μmol) in 4.0 mL of the 12.5% MAO solution in toluene. 5.0 μL of this solution was injected into the reactor and the reactor was heated to 80° C. The reactor was pressurized to 80 psig, with ethylene. At the end of one hour, the ethylene flow was stopped, the reactor was cooled to room temperature, and 100 mL of acidic methanol (1:1 mixture of 3M HCl/methanol) was added to the mixture to form a slurry. After stirring the slurry for 30 minutes, the polymer was filtered, washed with acetone, and dried overnight under vacuum. 8.0 g of the ethylene/1-octene copolymer was recovered having a $M_w$ of 166,500 and $M_w/M_n$ of 1.93. The copolymer had a density of 0.929, a melt index ratio ($I_{20}/I_2$) of 16.8 at 23° C., and contained 9.3 wt. % 1-octene by $^{13}C$ NMR.

EXAMPLE 10

In this example, ethylene and 1-octene monomers were copolymerized by first adding dry, oxygen-free toluene (180 mL) and 1-octene (20 mL) to the reactor of Example 5. 46 mL of triisobutylaluminum was added to the reactor. A catalyst solution was prepared by dissolving the 1:1 mixture of triphenylcarbenium chloride and $B(C_6F_5)_4^-[2\text{-}Me_2N^+(H)CH_2CH_2\text{—}C_5H_4]TiCl_3$ (15.3 mg, 12.2 μmol) in 4.0 mL of toluene. 1.0 mL of this solution was injected into the reactor and the reactor was heated to 80° C. The reactor was then pressurized to 80 psig with ethylene. At the end of one hour, the ethylene flow was stopped; the reactor was cooled to room temperature, and 100 mL of acidic methanol (1:1 mixture of 3M HCl/methanol) was added to form a slurry. After stirring the slurry for 30 minutes, the polymer was filtered, washed with acetone, and dried under vacuum overnight. 6.8 g of the ethylene/1-octene copolymer was isolated having a $M_w$ of 342,000 and $M_w/M_n$ of 3.29. The copolymer had a density of 0.903, and contained 40.1 wt. % 1-octene by $^{13}C$ NMR.

The invention has been described in detail with particular reference to preferred embodiments thereof, but it will be understood that variations and modifications other than as specifically described herein can be effected within the spirt and xcope of the appended claims. It is further to be understood that all references cited above are incorporated herein by reference.

We claim:

1. A cyclopentadienyl transition metal compound of the formula:

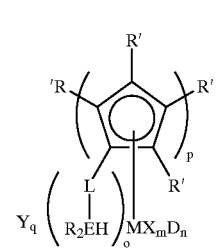

(I)

wherein,

M is a Group IV metal selected from the group consisting of titanium, zirconium and hafnium;

R' is each independently selected from the group consisting of hydrogen, hydrocarbyl groups, silyl groups, germyl groups, stannyl groups, and groups wherein two or more R' groups can be joined to form a ring;

L is a covalent bridging group containing a Group 14 element selected from the group consisting of carbon, silicon, germanium, and tin;

E is a Group 15 element selected from the group consisting of nitrogen, phosphorous, arsenic, and antimony;

Y is an anion that results in the compound being hydrocarbon soluble;

R is each independently selected from the group consisting of hydrocarbyl groups, silyl groups, groups wherein two R groups can be joined to form a ring, and groups wherein an L group and an R group can be joined to form a ring;

X is each independently selected from the group consisting of hydrogen, halides, hydrocarbyl groups, silyl groups, alkoxides, aryloxides, amides, arylamides, phosphides, arylphosphides, carboxylates, and sulfonates;

D is a neutral Lewis base;

m is one, two, or three, depending on the valency and oxidation state of M;

n is 0, 1, or 2;

o is 1;

p is 1 or 2;

q is 1 or 2; and $1 \leq q \leq p \leq o \leq 2$.

2. The compound according to claim 1 wherein Y is an anion selected from the group consisting of tetrakis (pentafluorophenyl)borate, tetrakis[3,5-(bistrifluoromethyl) phenyl]borate, tetrakis(2,3,4,5-tetrafluorophenyl)borate and tetrakis(2,3,5,6-tetrafluorophenyl)borate.

3. The compound according to claim 2 wherein Y is tetrakis (pentafluorophenyl)borate.

4. The compound according to claim 1 comprising $[(C_5H_4CH_2CH_2N[H]Me_2)TiCl_3]^+Y^-$ wherein Y is an anion that results in the compound being hydrocarbon soluble.

5. The compound according to claim 4 wherein Y is tetrakis(pentafluorophenyl)borate.

6. The compound according to claim 1 wherein the cyclopentadienyl transition metal compound is a monocyclopentadienyl transition metal compound.

7. The compound according to claim 6 wherein m is three.

8. The compound according to claim 1 wherein M is selected from the group consisting of titanium and zirconium.

9. The compound according to claim 8 wherein M is titanium.

10. The compound according to claim 1 wherein R' is each independently selected from the group consisting of hydrogen and $C_1$–$C_4$ alkyls.

11. The compound according to claim 10 wherein at least two R' groups are hydrogen.

12. The compound according to claim 10 wherein R' is hydrogen.

13. The compound according to claim 1 wherein L is a covalent bridging group selected from the group consisting of $CR"_2$, $CR"_2CR"_2$, $CR"_2CR"_2CR"_2$, and $CR"=CR"$, wherein R" is each independently selected from the group consisting of hydrogen, $C_1$–$C_{14}$ alkyl, and $C_1$–$C_{14}$ aryl.

14. The compound according to claim 13 wherein L is selected from the group consisting of $CR"_2$, $CR"_2 CR"_2$, and $CR"_2CR"_2CR"_2$, wherein R" is each independently selected from the group consisting of hydrogen and methyl.

15. The compound according to claim 14 wherein L is $CH_2CH_2$.

16. The compound according to claim 1 wherein E is selected from the group consisting of nitrogen and phosphorous.

17. The compound according to claim 16 wherein E is nitrogen.

18. The compound according to claim 1 wherein R is each independently selected from hydrocarbyl groups and groups wherein two R groups can be joined to form a ring.

19. The compound according to claim 1 wherein X is each independently selected from the group consisting of halides and alkoxides.

20. The compound according to claim 19 wherein X is each independently selected from the group consisting of chlorine and isopropoxide.

21. The compound according to claim 20 wherein X is chlorine.

22. The compound according to claim 1 wherein n is one or two, and D is selected from the group consisting of ethers and tetrahydrofuran.

23. The compound according to claim 1 wherein n is 0.

24. A process for preparing a cyclopentadienyl transition metal compound according to claim 1 comprising reacting a compound of the formula

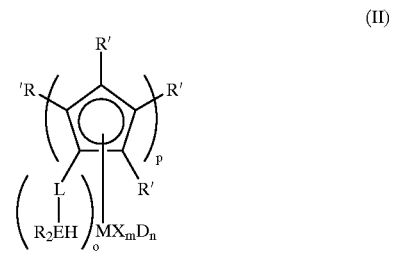

(II)

wherein,

M is a Group IV metal selected from the group consisting of titanium, zirconium and hafnium;

R' is each independently selected from the group consisting of hydrogen, hydrocarbyl groups, silyl groups, germyl groups, stannyl groups, and groups wherein two or more R' groups can be joined to form a ring;

L is a covalent bridging group containing a Group 14 element selected from the group consisting of carbon, silicon, germanium, and tin;

E is a Group 15 element selected from the group consisting of nitrogen, phosphorous, arsenic, and antimony;

R is each independently selected from the group consisting of hydrocarbyl groups, silyl groups, groups wherein two R groups can be joined to form a ring, and groups wherein an L group and an R group can be joined to form a ring;

X is each independently selected from the group consisting of hydrogen, halides, hydrocarbyl groups, silyl groups, alkoxides, aryloxides, amides, arylamides, phosphides, arylphosphides, carboxylates, and sulfonates;

D is a neutral Lewis base;

m is one, two, or three, depending on the valency and oxidation state of M;

n is 0, 1, or 2;

o is 1;

p is 1 or 2;

q is 1 or 2; and $1 \leq q \leq p \leq o \leq 2$;

with a Bronsted acid having a non-coordinating or weakly-coordinating anion.

25. The process according to claim 24 wherein the reaction is carried out in a solvent at a temperature ranging from about −100° C. to about 300° C.

26. The process according to claim 25 wherein the temperature ranges from about 25° C. to about 100° C.

27. The process according to claim 24 wherein the Bronsted acid is selected from $HB[3,5-(CF_3)C_6H_2]_4$, $HB(C_6F_5)_4$ and $C_6H_5NH_3$—$B(C_6F_5)_4$.

28. The process according to claim 25 wherein the solvent is a halogenated solvent.

29. A process for preparing a cyclopentadienyl transition metal compound according to claim 1 comprising reacting a compound of the formula:

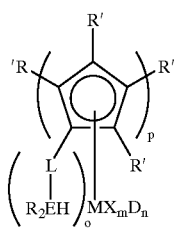

(II)

where
- M is a Group IV metal selected from the group consisting of titanium, zirconium and hafnium;
- R' is each independently selected from the group consisting of hydrogen, hydrocarbyl groups, silyl groups, germyl groups, stannyl groups, and groups wherein two or more R' groups can be joined to form a ring;
- L is a covalent bridging group containing a Group 14 element selected from the group consisting of carbon, silicon, germanium, and tin;
- E is a Group 15 element selected from the group consisting of nitrogen, phosphorous, arsenic, and antimony;
- Y is an anion that results in the compound being hydrocarbon soluble;
- R is each independently selected from the group consisting of hydrocarbyl groups, silyl groups, groups wherein two R groups can be joined to form a ring, and groups wherein an L group and an R group can be joined to form a ring;
- X is each independently selected from the group consisting of hydrogen, halides, hydrocarbyl groups, silyl groups, alkoxides, aryloxides, amides, arylamides, phosphides, arylphosphides, carboxylates, and sulfonates;
- D is a neutral Lewis base;
- m is one, two, or three, depending on the valency and oxidation state of M;
- n is 0, 1, or 2;
- o is 1;
- p is 1 or 2;
- q is 1 or 2; and
- $1 \leq q \leq p \leq o \leq 2$;

with a Bronsted acid to form an intermediate product of the formula:

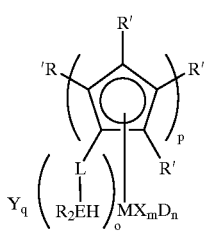

(III)

wherein,
- M is a Group IV metal selected from the group consisting of titanium, zirconium, and hafnium;
- R' is each independently selected from the group consisting of hydrogen, hydrocarbyl groups, silyl groups, germyl groups, stannyl groups and groups wherein two or more R' groups can be joined to form a ring;
- L is a covalent bridging group containing a Group 14 element selected from the group consisting of carbon, silicon, germanium, and tin;
- E is a Group 15 element selected from the group consisting of nitrogen, phosphorous, arsenic, and antimony;
- Y is an anion;
- R is each independently selected from the group consisting of hydrocarbyl groups, silyl groups, groups wherein two R groups can be joined to form a ring, and groups wherein an L group and an R group can be joined to form a ring;
- X is each independently selected from the group consisting of hydrogen, halides, hydrocarbyl groups, silyl groups, alkoxides, aryloxides, amides, arylamides, phosphides, arylphosphides, carboxylates, and sulfonates;
- D is a neutral Lewis base;
- m is one, two, or three, depending on the valency and oxidation state of M;
- n is 0, 1 or 2;
- o is 1;
- p is 1 or 2;
- q is 1 or 2; and
- $1 \leq q \leq p \leq o \leq 2$;

and reacting the intermediate product of the formula (III) with a salt of a non-coordinating or weakly-coordinating anion.

30. The process according to claim 29 wherein the reaction of the compound of formula (II) with the Bronsted acid is carried out in a solvent at a temperature ranging from about −100° C. to about 300° C., and the reaction of the intermediate product of formula (III) with the salt of a non-coordinating or weakly-coordinating anion is carried out in a solvent at a temperature ranging from about −100° C. to about 300° C.

31. The process according to claim 30 wherein each of the reactions is carried out at a temperature ranging from about 25° C. to about 100° C.

32. The process according to claim 29 wherein the Bronsted acid is selected from the group consisting of hydrogen halides, hydrogen sulfates, hydrogen phosphates and hydrogen nitrates.

33. The process according to claim 32 wherein the Bronsted acid is a hydrogen halide.

34. The process according to claim 29 wherein the salt of a non-coordinating or weakly-coordinating anion is selected from the group consisting of triphenylcarbenium tetrakis(pentafluorophenyl)borate, sodium tetrakis(pentafluorophenyl)borate, lithium tetrakis(pentafluorophenyl)borate, triphenylcarbenium tetrakis(3,5-trifluoromethylphenyl)borate and sodium tetrakis(3,5-trifluoromethylphenyl)borate.

35. A catalyst system comprising
(A) a cyclopentadienyl transition metal compound according to claim 1, and
(B) an activator selected from the group consisting of
(1) alumoxanes,
(2) a salt of a labile, non-coordinating or weakly-coordinating anion that can abstract one substituent X from the compound of (A),
(3) a neutral Lewis acid that can abstract one substituent X from the compound of (A), (4) an organometallic compound wherein the metal is selected from the group consisting of lithium, sodium, potassium, magnesium, calcium, zinc, boron and aluminum, and (5) mixtures of B(1) through B(4).

36. The catalyst system according to claim 35 wherein the compound of (A) is a monocyclopentadienyl transition metal compound according to claim 1.

37. The catalyst system according to claim 35 wherein the compound of (A) and the activator of (B) are present in a ratio of A/B ranging from about $10^0$ to about $10^6$.

38. The catalyst system according to claim 37 wherein the ratio of A/B ranges from about $10^2$ to about $10^5$.

39. The catalyst system according to claim 35 wherein the alumoxane of B(1) is methylalumoxane; the salt of a labile, non-coordinating or weakly-coordinating anion of B(2) is selected from the group consisting of borate salts and aluminate salts; the neutral Lewis acid of B(3) is selected from the group consisting of boranes and alanes; and the organometallic compound of B(4) is selected from the group consisting of alkyl boranes, alkyl aluminums, and alkyl zincs.

40. The catalyst system according to claim 39 wherein the organometallic compound of B(4) is a trialkyl aluminum.

41. The catalyst system according to claim 35 wherein the compound of (A) is a monocyclopentadienyl transition metal compound according to claim 1 having a borate anion and the activator of (B) is an aluminum alkyl.

42. The catalyst system according to claim 35 wherein the compound of (A) is supported on a support.

43. The catalyst system according to claim 42 wherein the support is selected from the group consisting of prepolymer, magnesium oxide, silica, alumina, and carbon black.

44. A process for producing polyolefins comprising (i) contacting at least one olefin, at a temperature and pressure and for a period of time sufficient to polymerize the olefin, with the catalyst system according to claim 35, and (ii) recovering the resulting polyolefin.

45. The process according to claim 44 wherein the temperature is from about 0° C. to about 300° C., the pressure is from about 1 atmosphere to about 1,500 atmospheres, and the period of time is from about 1 second to about 12 hours.

46. The process according to claim 44 wherein at least one of the olefins is an alpha olefin.

47. The process according to claim 46 wherein the alpha olefin is selected from the group consisting of $C_2$–$C_8$ alpha olefins.

48. The process according to claim 47 wherein the alpha olefin is ethylene or propylene.

49. The process according to claim 47 wherein the alpha olefin is selected from ethylene and $C_3$–$C_8$ comonomers, and propylene and $C_4$–$C_8$ comonomers.

50. The polyolefin produced by the process according to claim 44.

* * * * *